US008204286B2

(12) United States Patent
Sendai et al.

(10) Patent No.: US 8,204,286 B2
(45) Date of Patent: Jun. 19, 2012

(54) RADIATION IMAGE DETECTING SYSTEM, RADIATION IMAGE DETECTING METHOD, COMPUTER READABLE MEDIUM AND COMPUTER PROGRAM PRODUCT

(75) Inventors: Tomonari Sendai, Ashigarakami-gun (JP); Yasunori Ohta, Ashigarakami-gun (JP); Hiroaki Yasuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1170 days.

(21) Appl. No.: 12/026,647

(22) Filed: Feb. 6, 2008

(65) Prior Publication Data
US 2008/0187206 A1 Aug. 7, 2008

(30) Foreign Application Priority Data
Feb. 7, 2007 (JP) .................................. 2007-027931

(51) Int. Cl.
*G06K 9/00* (2006.01)
(52) U.S. Cl. ........................................ 382/128; 378/117
(58) Field of Classification Search .................. 382/128, 382/132; 378/62, 91, 98, 98.2, 98.5, 114–117, 378/162, 165, 204, 207
See application file for complete search history.

(56) References Cited

U.S. PATENT DOCUMENTS
7,532,942 B2 *   5/2009   Reiner ............................ 700/90
2006/0274145 A1 * 12/2006   Reiner ............................ 348/62

FOREIGN PATENT DOCUMENTS
| JP | 2003-33342 | A | 2/2003 |
| JP | 2003-210448 | A | 7/2003 |
| JP | 2003210448 | A | 7/2003 |
| JP | 2003310592 | A | 11/2003 |
| JP | 2005-342305 | A | 12/2005 |
| JP | 2005342305 | A | 12/2005 |

OTHER PUBLICATIONS
Japanese Patent Offie Action for Appln. No. 2007-027931; Jun. 21, 2011.

\* cited by examiner

*Primary Examiner* — Jurie Yun
(74) *Attorney, Agent, or Firm* — Sughrue Mion, PLLC

(57) ABSTRACT

A radiation image detecting system includes an image detecting information storing section storing thereon an image detecting condition under which a radiation image judged by a reader of the radiation image to be inappropriate is detected in association with a site whose radiation image is detected under the image detecting condition judged inappropriate, an image detecting information designating section designating, before a radiation image of an examined subject is detected, an image detecting condition under which the radiation image of the examined subject is detected and a site of the examined subject which is image-detected, and a warning section issuing an warning to a user when the image detecting condition designated by the image detecting information designating section falls within a predetermined range including an image detecting condition stored on the image detecting information storing section in association with the site designated by the image detecting information designating section.

12 Claims, 8 Drawing Sheets

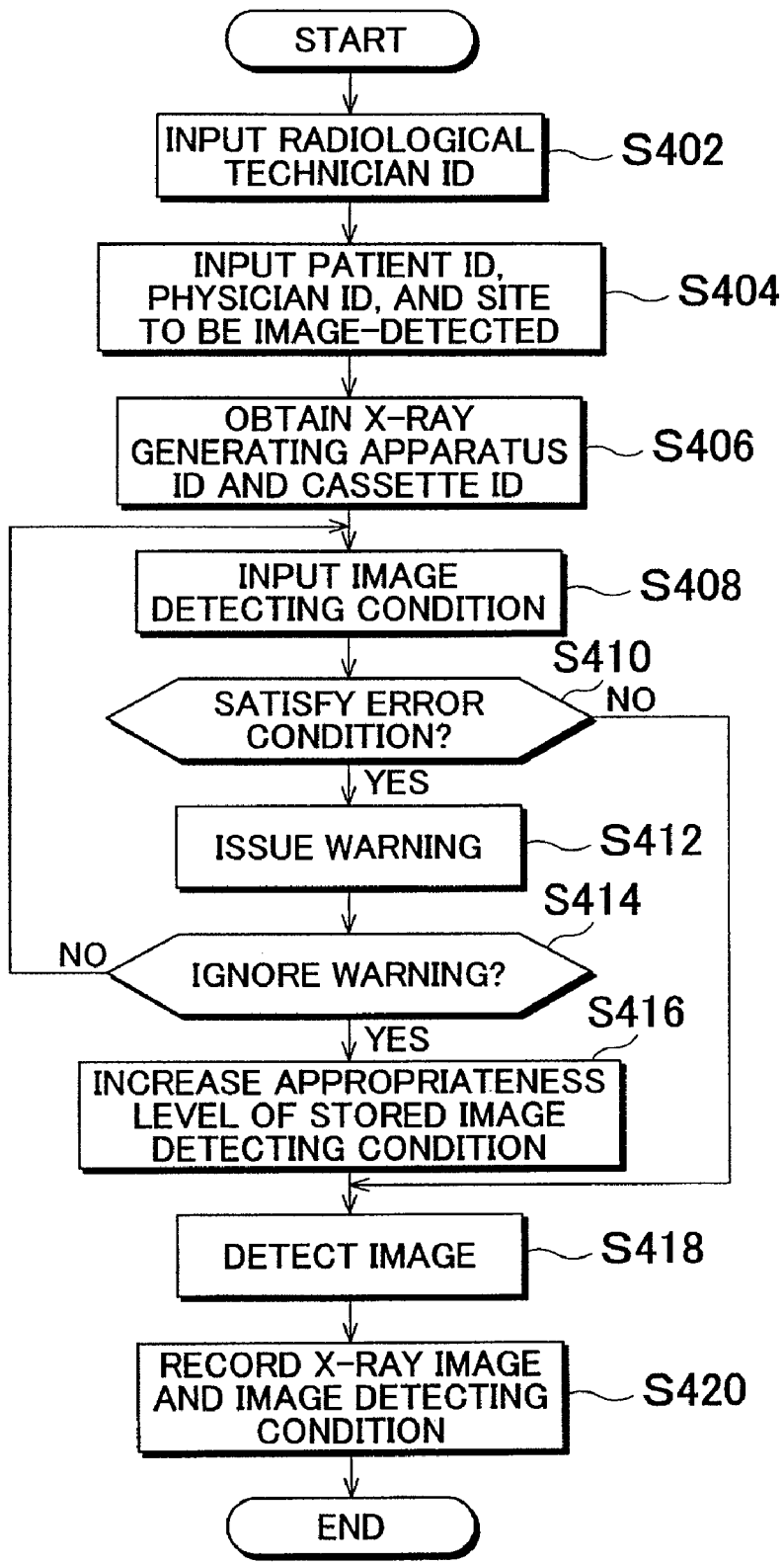
F I G . 4

200

| IMAGE DETECTING OPERATION ID | IMAGE DATA | PATIENT ID | RADIOLOGICAL TECHNICIAN ID | PHYSICIAN ID | X-RAY GENERATING APPARATUS ID | CASSETTE ID | IMAGE DETECTING CONDITION | SITE TO BE IMAGE-DETECTED | IMAGE DETECTING TIME | IMAGE DETECTING PLACE | APPROPRIATENESS LEVEL | NUMBER OF TIMES OF HIT |
|---|---|---|---|---|---|---|---|---|---|---|---|---|
| #501 | IMAGE DATA 501 | #511 | #521 | #531 | #551 | #561 | IMAGE DETECTING CONDITION A | SITE A | TIME A | PLACE A | 1 | 6 |
| #502 | IMAGE DATA 502 | #511 | #521 | #532 | #551 | #562 | IMAGE DETECTING CONDITION B | SITE B | TIME B | PLACE B | 2 | – |
| #503 | IMAGE DATA 503 | #512 | #521 | #533 | #552 | #562 | IMAGE DETECTING CONDITION C | SITE C | TIME C | PLACE C | 3 | – |
|  |  |  |  |  |  |  |  |  |  |  |  |  |

F I G . 5

280

| TUBE CURRENT | TUBE VOLTAGE | APERTURE DIAMETER | DURATION OF RADIATION | DISTANCE |
|---|---|---|---|---|
| TUBE CURRENT VALUE ± ΔI | TUBE VOLTAGE VALUE ± ΔV | APERTURE DIAMETER ± ΔD | DURATION OF RADIATION ± ΔT | DISTANCE ± L |

RADIATION IMAGE DETECTING SYSTEM, RADIATION IMAGE DETECTING METHOD, COMPUTER READABLE MEDIUM AND COMPUTER PROGRAM PRODUCT

CROSS REFERENCE TO RELATED APPLICATION

This patent application claims priority from a Japanese patent application No. 2007-027931 filed on Feb. 7, 2007, the contents of which are incorporated herein by reference.

BACKGROUND

1. Technical Field

The present invention relates to a radiation image detecting system, a radiation image detecting method, a computer readable medium and a computer program product. More particularly, the present invention relates to a radiation image detecting system and a radiation image detecting method for detecting radiation images, a computer readable medium storing thereon a program, and to a computer program product for use with the radiation image detecting system.

2. Related Art

A medical image detecting system is known and disclosed in Unexamined Japanese Patent Application Publication No. 2005-342305, for example. The medical image detecting system prestores thereon image detecting conditions used to detect breast images and cassette IDs of the cassettes used in association with the image detecting conditions. When an input image detecting order indicates that breasts are to be image-detected, the medical image detecting system reads a cassette ID associated with the image detecting condition included in the input image detecting order, and records thereon the image detecting order information and read cassette ID in association with each other. Apart from this, an examination system is known which identifies the type of a detection module at the time of image detecting, and issues warning when the identified type of the detection module is different from the type of an examination menu, for example, as disclosed in Unexamined Japanese Patent Application Publication No. 2003-210448.

Referring to radiation image detecting systems, there are cases where the position of the X-ray tube, the position of the detector, the position of the patient, the posture of the patient and other factors can not be adjusted freely, for example, a case where radiation images of the patient are detected while the patient stays lying on his/her own bed. According to the medical image detecting system disclosed in the publication No. 2005-342305, when the image detecting condition included in the image detecting order is changed adaptively at the actual image detecting occasion, the cassette recorded in association with the image detecting condition may not be capable of achieving appropriate image detecting. On the other hand, when the image detecting condition is set as instructed by the image detecting order, the detected image may not be appropriately used for diagnosis unless the positions of the patient and X-ray tube can be freely adjusted. Similarly, the images detected by the examination system disclosed in the publication No. 2003-210448 may not be appropriately used for diagnosis.

SUMMARY

Therefore, it is an object of an aspect of the innovations herein to provide a radiation image detecting system, a radiation image detecting method, a computer readable medium, and a computer program product which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary radiation image detecting system may include a radiation image detecting system including an image detecting information storing section that stores thereon an image detecting condition under which a radiation image which is judged by a reader of the radiation image to be inappropriate is detected, an image detecting information designating section that, before a radiation image of an examined subject is detected, designates an image detecting condition under which the radiation image of the examined subject is to be detected, and a warning section that issues warning to a user when the image detecting condition designated by the image detecting information designating section falls within a predetermined range including the image detecting condition stored on the image detecting information storing section.

The radiation image detecting system may further include a condition storing section that stores thereon a condition required to be satisfied by an image detecting condition which falls within the predetermined range including the image detecting condition stored on the image detecting information storing section. Here, when the image detecting condition designated by the image detecting information designating section satisfies the condition stored on the condition storing section, the warning section may issue warning to the user.

The image detecting information storing section may store thereon the image detecting condition which is judged to be inappropriate, in association with the radiation image which is detected under the image detecting condition judged inappropriate. When the image detecting condition designated by the image detecting information designating section falls within the predetermined range including the image detecting condition stored on the image detecting information storing section, the warning section may additionally present, for a radiologist or technologist, the radiation image stored on the image detecting information storing section in association with the image detecting condition.

According to the second aspect related to the innovations herein, one exemplary radiation image detecting method may include a radiation image detecting method including storing an image detecting condition under which a radiation image which is judged by a reader of the radiation image to be inappropriate is detected, before a radiation image of an examined subject is detected, designating an image detecting condition under which the radiation image of the examined subject is to be detected, and issuing warning to a user when the image detecting condition designated in the designating falls within a predetermined range including the image detecting condition stored in the storing.

According to the third aspect related to the innovations herein, one exemplary computer readable medium may include a computer readable medium storing thereon a program for use with a radiation image detecting apparatus. Here, the program causes the radiation image detecting apparatus to function as an image detecting information storing section that stores thereon an image detecting condition under which a radiation image which is judged by a reader of the radiation image to be inappropriate is detected, an image detecting information designating section that, before a radiation image of an examined subject is detected, designates an image detecting condition under which the radiation image of the examined subject is to be detected, and a warning section that issues warning to a user when the image detecting condition designated by the image detecting information designating section falls within a predetermined range including the image detecting condition stored on the image detecting information storing section.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

The present invention can provide a radiation image detecting system which can achieve a lower probability of unsuccessful image detecting attempts.

BRIEF DESCRIPTION OF THE DRAWINGS

FIG. 4 illustrates an exemplary flow of detecting a radiation image.

FIG. 5 illustrates, by using a table, exemplary data stored on an image detecting information storing section 200.

FIG. 6 illustrates, by using a table, exemplary data stored on a condition storing section 280.

DESCRIPTION OF EXEMPLARY EMBODIMENT

Some aspects of the invention will now be described based on an embodiment, which does not intend to limit the scope of the present invention, but exemplify the invention. All of the features and the combinations thereof described in the embodiment are not necessarily essential to the invention.

Figure 1:
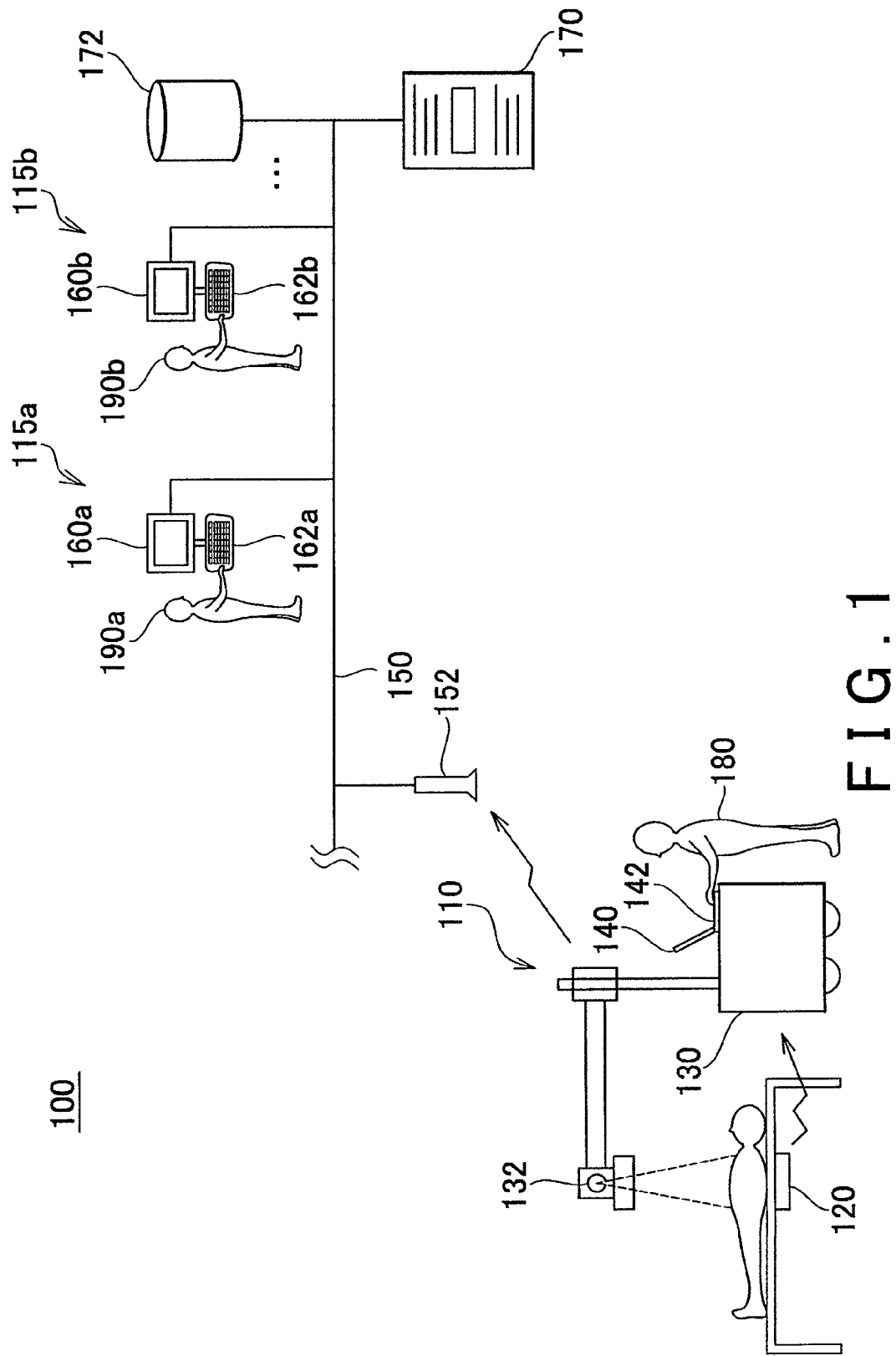
FIG. 1 illustrates an exemplary environment in which a radiation image detecting system 100 is used.

FIG. 1 illustrates an exemplary environment in which a radiation image detecting system 100 relating to an embodiment of the present invention is used. The radiation image detecting system 100 includes therein a radiation image detecting apparatus 110, a communication path 150, a wireless communication apparatus 152, diagnosis apparatuses 115a and 115b (hereinafter collectively referred to as the diagnosis apparatus 115), a server 170, and a database 172. The radiation image detecting apparatus 110 includes therein a cassette 120 and a radiation generating apparatus 130. The radiation generating apparatus 130 includes therein a monitor 140, an input apparatus 142 and a radiation source 132.

The diagnosis apparatus 115a includes therein a monitor 160a and an input apparatus 162a, and the diagnosis apparatus 115b includes therein a monitor 160b and an input apparatus 162b. Hereinafter, the monitors 160a and 160b are collectively referred to as the monitor 160, and the input apparatuses 162a and 162b are collectively referred to as the input apparatus 162. Although FIG. 1 shows only a single radiation image detecting apparatus 110 for various limitations, the radiation image detecting system 100 may include more than one radiation image detecting apparatus 110.

The database 172 stores thereon a radiation image detected by the radiation image detecting apparatus 110, an image detecting condition used when the radiation image is detected, and appropriateness level information indicating the level of appropriateness of the image detecting condition used when the radiation image is detected, in association with each other. The appropriateness level information may be input by a radiological technician 180 when the radiation image is detected by the radiation image detecting apparatus 110, or may be input by physicians 190a and 190b (hereinafter collectively referred to as the physician 190) via the input apparatus 162 when the physician 190 reads the radiation image by means of the diagnosis apparatus 115.

The following describes the flow of detecting a new radiation image of an examined subject. The server 170 receives image detecting information regarding a patient, which is input by the physician 190 via the input apparatus 162. The image detecting information includes a distinguishable identification (ID) of the patient, the name, age, sex and weight of the patient, the site to be image-detected, and image detecting direction (such as P→A and L→R). The server 170 then generates an image detecting order including the information provided by the image detecting information and a physician ID identifying the physician 190.

The radiation image detecting apparatus 110 detects a radiation image of the patient in accordance with the manipulation of the radiological technician 180. The radiation image detecting apparatus 110 may be mobile. Therefore, the radiation image detecting apparatus 110 may detect a radiation image in accordance with the manipulation of the radiological technician 180 in the patient's room at the hospital or at the patient's own home. Before starting to image-detect the patient, the radiation image detecting apparatus 110 obtains, from the server 170, the image detecting order issued for the patient, via the wireless communication apparatus 152 provided in the vicinity of the communication path 150 and radiation image detecting apparatus 110. Resultantly, the monitor 140 displays thereon the patient ID, the name, age, sex and weight of the patient, the site to be image-detected, the image detecting direction and the physician ID included in the image detecting order.

The radiological technician 180 determines an image detecting condition based on the age, sex, weight, the site to be image-detected and the like which are displayed on the monitor 140, and inputs the determined image detecting condition via the input apparatus 142. Here, the image detecting condition includes the tube current, the tube voltage, the aperture diameter of the radiation source 132, the duration of radiation, the distance between the radiation source 132 and the patient, and the distance between the radiation source 132 and the cassette 120. Alternatively, the radiation image detecting apparatus 110 may receive the image detecting condition from the server 170. The radiological technician 180 then adjusts the positions of the cassette 120, the patient and the radiation source 132 in compliance with the determined image detecting condition. The radiological technician 180 subsequently inputs via the input apparatus 142 information indicating that all the arrangements have been made for the image detecting operation. On reception of the information indicating that all the arrangements have been made for the image detecting operation, the radiation image detecting apparatus 110 measures the distance between the radiation source 132 and the patient and the distance between the radiation source 132 and the cassette 120, and transmits, to the server 170, the measured distances and the image detecting condition including the tube current, the tube voltage, the aperture diameter of the radiation source 132, the duration of radiation.

When receiving the image detecting condition from the radiation image detecting apparatus 110, the server 170 extracts, from the image database 172, an image detecting condition stored in association with a level of appropriateness indicating inappropriateness, and compares the extracted image detecting condition with the image detecting condition received from the radiation image detecting apparatus 110. When the degree of match between the image detecting condition received from the radiation image detecting apparatus 110 and the image detecting condition associated with the inappropriateness information is higher than a predetermined degree of match, the server 170 notifies the radiation image detecting apparatus 110 of an error. When receiving the notification indicating an error from the server 170, the radiation image detecting apparatus 110 causes the monitor 140 to display thereon information indicating that the image detecting condition is inappropriate, to issue an warning to the radiological technician 180. In this way, the radiation image detecting system 100 can achieve a lower probability that the radiological technician 180 detects a radiation image under an inappropriate image detecting condition. Furthermore, when the warning is displayed, the reason why the warning is issued (such as the amount of radiation is insufficient and the level for the tube voltage is inappropriate (too high or too low)) may be also displayed. In this way, the radiological technician 180 can easily understand the reason why the warning is issued, which makes it easier for the radiological technician 180 to change the image detecting condition.

The cassette 120 may include an imaging plate with a photostimulable phosphor, and a radiation film sensitive to radiation (including an intensifying screen). The cassette 120 is used to detect radiation images of the patient. The cassette 120 is shown as an example of a radiation detector used for detecting radiation images. As the radiation detector, diverse devices including a solid radiation detector such as an FPD may be used. According to the present embodiment, the radiation may be an X-ray, electromagnetic radiation such as gamma radiation, or particle radiation such as alpha radiation. The radiation image detecting apparatus 110 may be a tomographic image detecting apparatuses such as a CT apparatus, but the image detecting method for the radiation image detecting apparatus 110 is not limited to such.

Figure 2:
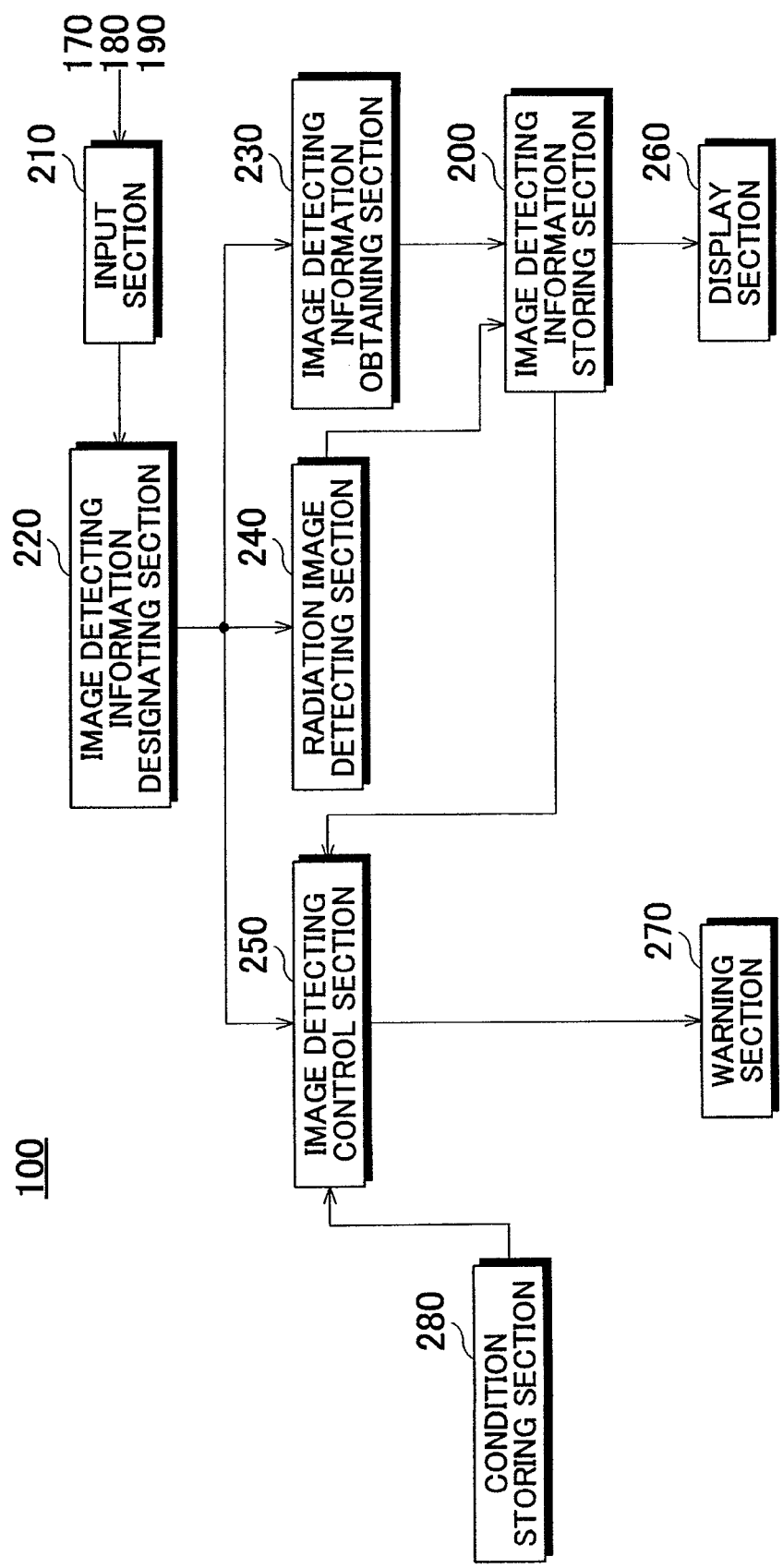
FIG. 2 illustrates an exemplary block configuration of the radiation image detecting system 100.

FIG. 2 illustrates an exemplary block configuration of the radiation image detecting system 100. The radiation image detecting system 100 includes therein an image detecting information storing section 200, an input section 210, an image detecting information designating section 220, an image detecting information obtaining section 230, a radiation image detecting section 240, an image detecting control section 250, a display section 260, a warning section 270, and a condition storing section 280. The input apparatuses 142 and 162 are shown as an example of the input section 210. The monitors 140 and 160 are shown as an example of the display section 260. The database 172 is shown as an example of the image detecting information storing section 200. The server 170 may include therein the image detecting control section 250.

The radiation image detecting section 240 detects a radiation image by means of radiation passing through an examined subject. For example, the radiation image detecting section 240 may detect an X-ray image by means of an X-ray passing through the examined subject. Here, the X-ray image is mentioned as an example of the radiation image. The image detecting information obtaining section 230 obtains the image detecting condition for the radiation image-detected by the radiation image detecting section 240. For example, the image detecting information obtaining section 230 may obtain the image detecting condition designated by the radiological technician 180 at the X-ray generating apparatus, or obtain the image detecting condition included in the image detecting order information. The display section 260 displays thereon the radiation image-detected by the radiation image detecting section 240.

The input section 210 receives, from a user, inappropriateness information indicating that the image detecting condition for the radiation image-detected by the radiation image detecting section 240 is inappropriate. For example, the input section 210 receives, from a reader of the radiation image, the inappropriateness information indicating that the image detecting condition for the radiation image-detected by the radiation image detecting section 240 is inappropriate. Here, the reader of the radiation image includes the radiological technician 180 and the physician 190. For example, when judging that the image detecting condition is inappropriate based on what is shown by the radiation image displayed on the monitor 140, the radiological technician 180 inputs the inappropriateness information by utilizing the information input function provided by the input apparatus 142 or the touch panel function provided by the monitor 140. As another example, when judging that the image detecting condition is inappropriate based on what is shown by the radiation image displayed on the display section 260, the physician 190 inputs the inappropriateness information by utilizing the information input function provided by the input apparatus 162 or the touch panel function of the monitor 160. When the input section 210 receives the inappropriateness information, the image detecting information storing section 200 stores thereon the image detecting condition obtained by the image detecting information obtaining section 230. In the above-described manner, the image detecting information storing section 200 stores thereon the image detecting condition under which the radiation image that is judged inappropriate by the reader of the radiation image is detected.

The image detecting information designating section 220 designates an image detecting condition under which a radiation image of an examined subject is to be detected, before the radiation image of the examined subject is detected. The image detecting control section 250 judges whether the image detecting condition designated by the image detecting information designating section 220 falls within a predetermined range that includes the image detecting condition stored on the image detecting information storing section 200. When the image detecting control section 250 judges that the image detecting condition designated by the image detecting information designating section 220 falls within the predetermined range including the image detecting condition stored on the image detecting information storing section 200, the warning section 270 issues warning to the user. Here, the monitor 140 may be an example of the warning section 270, and display thereon the warning information issued for the user.

The image detecting information storing section 200 stores thereon a plurality of image detecting conditions which have been judged inappropriate. In this case, when the image detecting condition designated by the image detecting information designating section 220 falls within the range indicated by the plurality of image detecting conditions stored on the image detecting information storing section 200, the warning section 270 may issue warning to the user. For example, when the image detecting information storing section 200 stores thereon 40 kV, 42 kV and 44 kV, the warning section 270 may issue warning to the user when the tube voltage designated by the image detecting information designating section 220 falls within the range from 40 kV to 44 kV.

The condition storing section 280 stores thereon a condition required to be satisfied by an image detecting condition that falls within the predetermined range that includes the image detecting condition stored on the image detecting information storing section 200. When the image detecting condition designated by the image detecting information designating section 220 satisfies the condition stored on the condition storing section 280, the warning section 270 issues warning to the user. Here, the image detecting information storing section 200 stores thereon the image detecting conditions that have been judged inappropriate in association with the radiation images which are detected under the inappropriate image detecting conditions. When the image detecting condition designated by the image detecting information designating section 220 falls within a predetermined range including a given image detecting condition stored on the image detecting information storing section 200, the warning section 270 also presents, to the radiologist or technologist, the radiation image stored on the image detecting information storing section 200 in association with the given image detecting condition.

The image detecting information designating section 220 designates the image detecting condition under which the radiation image of the examined subject is to be detected and the site of the examined subject which is to be image-detected, before the radiation image of the examined subject is detected. Here, the image detecting information storing section 200 stores thereon the image detecting conditions that have been judged inappropriate in association with the sites whose radiation images are detected under the inappropriate image detecting conditions. When the image detecting condition designated by the image detecting information designating section 220 falls within a predetermined range including the image detecting condition stored on the image detecting information storing section 200 in association with the site designated by the image detecting information designating section 220, the warning section 270 issues warning to the user.

The image detecting information designating section 220 designates the image detecting condition under which the radiation image of the examined subject is detected and examined subject identifying information identifying the examined subject, before the radiation image of the examined subject is detected. Here, the image detecting information storing section 200 stores thereon the image detecting conditions that have been judged inappropriate in association with pieces of examined subject identifying information identifying the examined subjects whose radiation images are detected under the inappropriate image detecting conditions. When the image detecting condition designated by the image detecting information designating section 220 falls within a predetermined range including the image detecting condition stored on the image detecting information storing section 200 in association with the examined subject identifying information designated by the image detecting information designating section 220, the warning section 270 issues warning to the user.

The image detecting information designating section 220 designates radiologist/technologist identifying information that identifies the radiologist or technologist who takes the radiation image of the examined subject, before the radiation image of the examined subject is detected. Here, the image detecting information storing section 200 stores thereon the image detecting conditions that have been judged inappropriate in association with pieces of radiologist/technologist identifying information identifying the radiologists or technologists who take the radiation images under the inappropriate image detecting conditions. When the image detecting condition designated by the image detecting information designating section 220 falls within a predetermined range including the image detecting condition stored on the image detecting information storing section 200 in association with the radiologist/technologist identifying information designated by the image detecting information designating section 220, the warning section 270 issues warning to the user.

The image detecting information designating section 220 designates image detecting device identifying information identifying the image detecting device that detects the radiation image of the examined subject, before the radiation image of the examined subject is detected. Here, the image detecting information storing section 200 stores thereon the image detecting conditions that have been judged inappropriate in association with pieces of image detecting device identifying information identifying the image detecting devices that detect radiation images under the inappropriate image detecting conditions. When the image detecting condition designated by the image detecting information designating section 220 falls within a predetermined range including the image detecting condition stored on the image detecting information storing section 200 in association with the image detecting device identifying information designated by the image detecting information designating section 220, the warning section 270 issues warning to the user.

Furthermore, when the input section 210 receives the inappropriateness information, the image detecting information storing section 200 stores thereon the image detecting condition obtained by the image detecting information obtaining section 230 in association with reader identifying information identifying the reader who inputs the inappropriateness information. Before the radiation image of the examined subject is newly detected, the image detecting information designating section 220 designates reader identifying information identifying the reader who is to read and interpret the new radiation image. When the image detecting condition designated by the image detecting information designating section 220 falls within a predetermined range including the image detecting condition stored on the image detecting information storing section 200 in association with the reader identifying information designated by the image detecting information designating section 220, the warning section 270 issues warning to the user.

As described in the above section, the radiation image detecting system 100 issues warning to the radiological technician 180 when the radiological technician 180 attempts to detect a radiation image under an image detecting condition similar to image detecting conditions under which unsuccessful radiation images were detected. Having such a configuration, the radiation image detecting system 100 can achieve a lower probability of unsuccessful image detecting attempts. As a result, the present embodiment can reduce the probability that the radiological technician 180 is required to detect another radiation image of the same examined subject, thereby enabling the radiological technician 180 to efficiently perform the image detecting operation. If the image detecting attempts fail, the patient and radiological technician 180 are exposed to the radiation in vain. The present embodiment can prevent this from occurring. Here, the examined subject is a subject whose images are to be detected by using radiation. The examined subject includes human beings and animals which are examined and diagnosed by using radiation, and industrial products which are tested in a nondestructive manner by using radiation.

Figure 3:
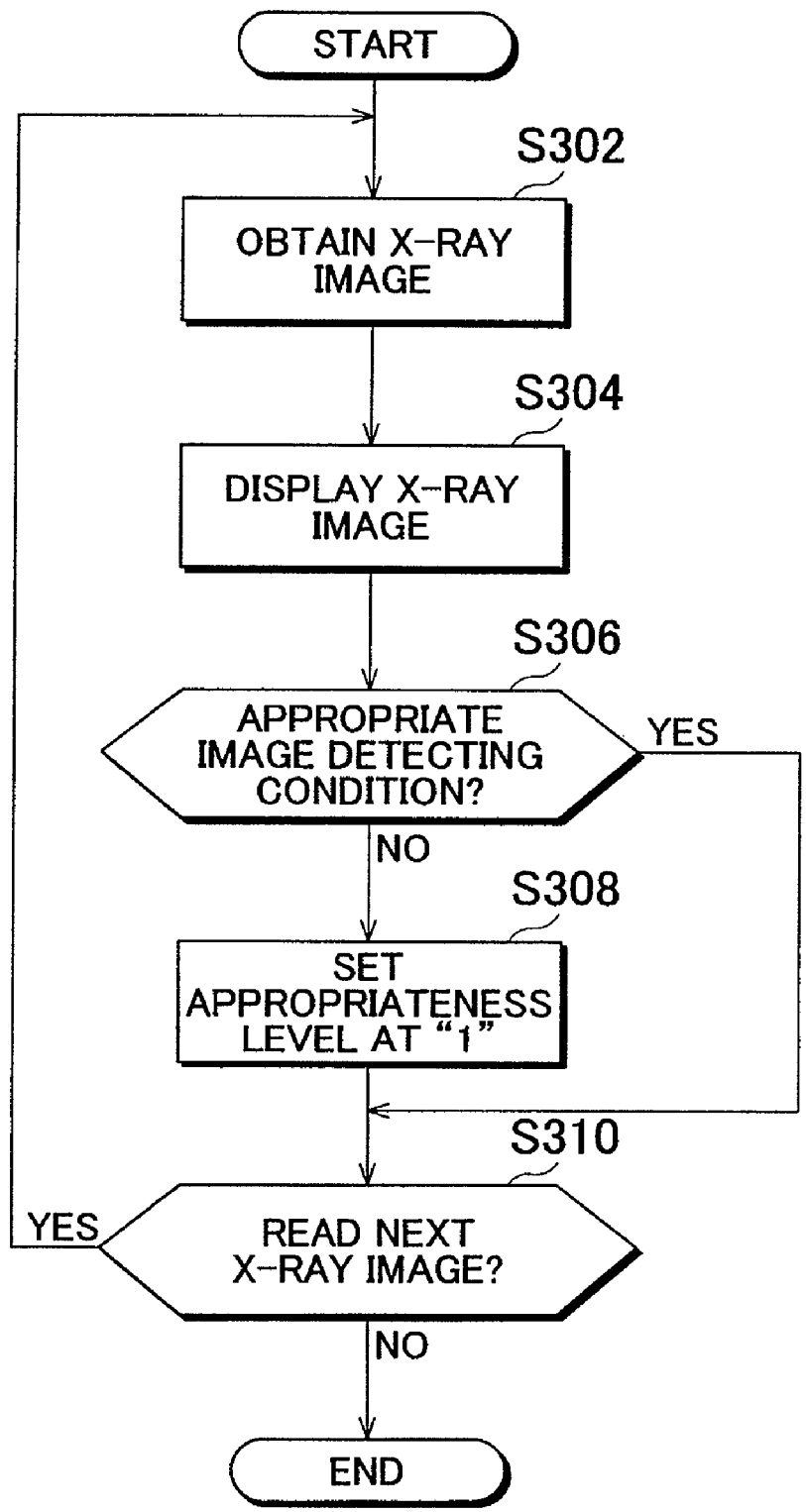
FIG. 3 illustrates an exemplary flow of reading a radiation image.

FIG. 3 illustrates an exemplary flow of reading a radiation image at the radiation image detecting system 100. According to the radiation image detecting system 100, both the radiological technician 180 and physician 190 can read the radiation image and input inappropriateness information. The following describes, as an example, how the physician 190 reads the radiation image.

The diagnosis apparatus 115 obtains an X-ray image in response to an instruction made by the physician 190 (step S302). The monitor 160 displays thereon the X-ray image (step S304). In the step S302, the diagnosis apparatus 115 may additionally obtain the image detecting condition attached to the X-ray image. In the step S304, the monitor 160 may additionally display thereon the obtained image detecting condition together with the X-ray image. The physician 190 then observes what is shown by the X-ray image displayed on the monitor 160, to judge whether the image detecting condition is appropriate. When judging that the image detecting condition is inappropriate, the physician 190 inputs inappropriateness information, for example, by using the input apparatus 162. The inappropriateness information indicates the appropriateness level of "1". In this way, the appropriateness level of "1" is input into the radiation image detecting system 100 via the input section 210, and the appropriateness level of "1" is attached to the X-ray image, which is stored on the image detecting information storing section 200 (step S308). The monitor 160 then displays thereon a question asking whether the next X-ray image is to be read. When the physician 190 inputs information indicating that the next X-ray image is to be read, the radiation image detecting system 100 moves to the operation in the step S302. When the physician 190 inputs information indicating that the next X-ray image is not to be read, the radiation image detecting system 100 ends the procedure.

When judging that the image detecting condition is appropriate in the step S306, the physician 190 may input, via the input section 210, the appropriateness level indicating the level of the appropriateness of the image detecting condition under which the X-ray image is detected. In this case, the image detecting information storing section 200 may store thereon the appropriateness level input via the input section 210 in association with the X-ray image and image detecting condition. Note that the appropriateness level will be described with reference to FIG. 5. In the above-described manner, the image detecting information storing section 200 stores thereon the image detecting condition judged to be inappropriate in association with the inappropriateness information.

FIG. 4 illustrates an exemplary flow of detecting a radiation image performed by the radiation image detecting system 100. The radiological technician 180 inputs a radiological technician ID via the input section 210 before starting the image detecting operation. The radiological technician 180 further inputs, into the radiation generating apparatus 130 via the input section 210, a patient ID as an example of the examined subject identifying information, a physician ID as an example of the reader identifying information and the site to be image-detected. Note that the patient ID, the physician ID and the site to be image-detected may be input into the radiation generating apparatus 130 based on the image detecting order. The radiation generating apparatus 130 subsequently obtains an X-ray apparatus ID identifying the radiation generating apparatus 130 and a cassette ID identifying the cassette 120 (step S406). The radiation image detecting apparatus 110 may obtain the X-ray apparatus ID and cassette ID which are respectively stored on the memory of the radiation generating apparatus 130 and the memory of the cassette 120.

The radiological technician 180 designates the image detecting condition by inputting the image detecting condition via the input section 210 (step S408). Here, the image detecting condition included in the image detecting order obtained by the image detecting information obtaining section 230 may be designated onto the image detecting information designating section 220. Also, the radiological technician 180 may change the designated image detecting condition via the input section 210, depending on the image detecting circumstances such as the position of the patient and the position of the radiation source 132. The image detecting control section 250 then judges whether the image detecting condition designated by the image detecting information designating section 220 satisfies an error condition (step S410). To be specific, when the relation between the image detecting condition designated by the image detecting information designating section 220 and the image detecting condition stored on the image detecting information storing section 200 satisfies the condition stored on the condition storing section 280, the image detecting control section 250 judges that the image detecting condition designated by the image detecting information designating section 220 satisfies the error condition.

When the image detecting control section 250 judges in the step S410 that the image detecting condition designated by the image detecting information designating section 220 satisfies the error condition, the warning section 270 displays a warning message (step S412). Here, the monitor 140 may be an example of the warning section 270. If such is the case, the monitor 140 displays thereon the warning message.

The radiological technician 180 then decides whether to continue the image detecting operation (step S414). When the radiological technician 180 decides to terminate the image detecting operation, the radiation image detecting apparatus 110 moves to the operation in the step S408, and causes the radiological technician 180 to input a different image detecting condition.

When deciding to continue the image detecting operation, the radiological technician 180 inputs via the input section 210 information indicating that the image detecting operation is to be continued. When the radiation image detecting system 100 receives, via the input section 210, the information that the image detecting operation is to be continued, the image detecting information storing section 200 increases the appropriateness level associated with the image detecting condition which is stored on the image detecting information storing section 200 and whose relation with the image detecting condition designated by the image detecting information designating section 220 is judged to satisfy the condition stored on the condition storing section 280 (step S416). The radiation image detecting apparatus 110 then detects a radiation image of the patient (step S418). The image detecting information storing section 200 stores thereon the image detecting condition under which the radiation image of the patient is detected in the step S418, in association with the X-ray image (step S420). To be specific, the server 170 obtains the image detecting condition under which the X-ray image is detected and the X-ray image from the radiation image detecting apparatus 110, and stores the obtained image detecting condition and X-ray image on the database 172 in such a manner that the image detecting condition is attached to the X-ray image.

FIG. 5 illustrates, by using a table, exemplary data stored on the image detecting information storing section 200. The image detecting information storing section 200 stores thereon, in association with each other, an image detecting operation ID indicating identification information identifying a detected X-ray image, image data indicating the image data of the X-ray image, a patient ID identifying a patient to whom the X-ray image belongs, a radiological technician ID identifying the radiological technician 180, a physician ID identifying the physician 190, an X-ray apparatus ID identifying the radiation source, a cassette ID identifying the X-ray detector, an image detecting condition indicating the image detecting condition data, a site indicating the site that has been image-detected, an image detecting time indicating the time at which the X-ray image is detected, an image detecting place indicating the place at which the X-ray image is detected, an appropriateness level input by the physician 190 or radiological technician 180, and the number of times of hit indicating the number of times at which the condition is satisfied.

The X-ray apparatus ID may be information identifying the radiation source 132. Here, the radiation image detecting system 100 can use a variety of radiation detectors for detecting the radiation, other than the cassette 120. Therefore, the cassette ID is only shown as an example of the information identifying the radiation detector used in the radiation image detecting system 100. The site may be information identifying the site of the patient's body such as the chest region and cervical spine which has been image-detected. The image detecting time may indicate a date and a time. The image detecting place may be information identifying the place at which the image is detected, such as the room number and the bed number. The image detecting condition includes the distance between the radiation source 132 and the examined subject, the distance between the radiation source 132 and the cassette 120, the duration of the radiation, and the aperture diameter of the radiation source 132. When the radiation source 132 is the X-ray source, the image detecting condition may include the tube current and tube voltage of the X-ray source.

The image detecting information storing section 200 stores thereon the appropriateness level indicating one of three different levels indicating the appropriateness of the image detecting condition. To be specific, "1" indicates that the image detecting condition is inappropriate, and "2" and "3" both indicate that the image detecting condition is appropriate. Note that the image detecting condition is more appropriate when associated with the appropriateness level of "3" than when associated with "2". In this way, each image detecting condition stored on the image detecting information storing section 200 is associated with one of the plurality of levels indicating the appropriateness of the image detecting condition.

Here, it is assumed that the image detecting control section 250 judges that the image detecting condition designated by the image detecting information designating section 220 falls within the range which is stored on the condition storing section 280 and includes the image detecting condition stored on the image detecting information storing section 200. As described with reference to the step S416, when the radiological technician 180 inputs, via the input section 210, the information indicating that the image detecting operation is to be continued, the image detecting information storing section 200 increases the appropriateness level stored thereon in association with the image detecting condition. For example, even when the image detecting condition designated by the image detecting information designating section 220 is judged to fall within the range which is stored on the condition storing section 280 and includes the image detecting condition A stored on the image detecting information storing section 200, the image detecting information storing section 200 increases the appropriateness level stored thereon in association with the image detecting condition A from "1" to "2" under the condition that the radiological technician 180 inputs via the input section 210 the information indicating that the image detecting operation is to be continued. Here, consider the case where the image detecting condition A is mistakenly stored as an inappropriate image detecting condition on the image detecting information storing section 200 even though the image detecting condition A is actually an appropriate image detecting condition, for example. In this case, if the radiological technician 180 ignores the warning issued, judges that the image detecting condition is actually appropriate, and decides to continue the image detecting operation, the warning is repeatedly issued because of the image detecting condition A. The above-mentioned configuration can prevent such a problem from occurring.

The number of times of hit indicates the number of times at which the image detecting condition designated by the image detecting information designating section 220 is judged to fall within the range which is stored on the condition storing section 280 and includes the image detecting condition stored on the image detecting information storing section 200. For example, when the image detecting condition designated by the image detecting information designating section 220 is judged to fall within the range which is stored on the condition storing section 280 and includes the image detecting condition A stored on the image detecting information storing section 200, the image detecting information storing section 200 increments the value indicated by the number of times of hit which is stored in association with the image detecting condition A.

FIG. 6 illustrates, by using a table, exemplary data stored on the condition storing section 280. The condition storing section 280 stores thereon the ranges for the tube current, the tube voltage, the aperture diameter, the duration of the radiation, and the distance. Here, these items are included in the image detecting condition. For example, the condition storing section 280 stores thereon the value "ΔI" as the range for the tube current, which is stored on the image detecting information storing section 200. Here, a case is assumed that the image detecting information storing section 200 stores thereon the tube current value "I" as the image detecting condition, for example. When the tube current value designated by the image detecting information designating section 220 falls within the range that has a variation of ΔI from the tube current value "I", that is to say, the range from (I−ΔI) to (I+ΔI), the image detecting control section 250 judges that the image detecting condition designated by the image detecting information designating section 220 satisfies the condition stored on the condition storing section 280.

The image detecting control section 250 may judge that the image detecting condition designated by the image detecting information designating section 220 satisfies the condition stored on the condition storing section 280, when all of the values of the tube current, tube voltage, aperture diameter, radiation duration and distance which are designated by the image detecting information designating section 220 respectively fall within the ranges that are defined by the values stored on the condition storing section 280 and the values of the tube current, tube voltage, aperture diameter, radiation duration and distance which are stored on the image detecting information storing section 200, or alternatively when any one of the values of the tube current, tube voltage, aperture diameter, radiation duration and distance which are designated by the image detecting information designating section 220 falls within the corresponding one of the ranges that are defined by the values stored on the condition storing section 280.

When the image detecting condition designated by the image detecting information designating section 220 falls within the range which is stored on the condition storing section 280 and includes the image detecting condition stored on the image detecting information storing section 200 in association with the appropriateness level of "2" or "3" (for example, the image detecting condition B or C), the display section 260 may display thereon the appropriateness level stored on the image detecting information storing section 200 in association with the image detecting condition, so as to notify the radiological technician 180 of the appropriateness level.

When the value of the number of times of hit which is stored on the image detecting information storing section 200 in association with a given image detecting condition is larger than a predetermined value, the image detecting control section 250 may judge that the image detecting condition designated by the image detecting information designating section 220 satisfies the condition stored on the condition storing section 280 when the image detecting condition designated by the image detecting information designating section 220 falls within an image detecting condition indicating a larger range than the range which is stored on the condition storing section 280 and includes the given image detecting condition. As the value of the number of times of hit which is stored on the image detecting information storing section 200 in association with a given image detecting condition increases, the image detecting control section 250 may judge that the image detecting condition designated by the image detecting information designating section 220 satisfies the condition stored on the condition storing section 280 when the image detecting condition designated by the image detecting information designating section 220 falls within an image detecting condition which indicates an accordingly increased range and includes the given image detecting condition.

As previously discussed, the radiation image detecting system 100 issues warning when an attempt is made to detect a radiation image under an image detecting condition similar to an image detecting condition that has been judged to be inappropriate. Having this configuration, the radiation image detecting system 100 can prevent the user from making the same mistake. Since the image detecting information storing section 200 stores thereon the appropriateness level in association with the x-ray apparatus ID and physician ID, the radiological technician 180 can take into consideration the preference of the physician 190 and the particular problems of the radiation image detecting apparatus 110 when designating the image detecting condition.

Figure 7:
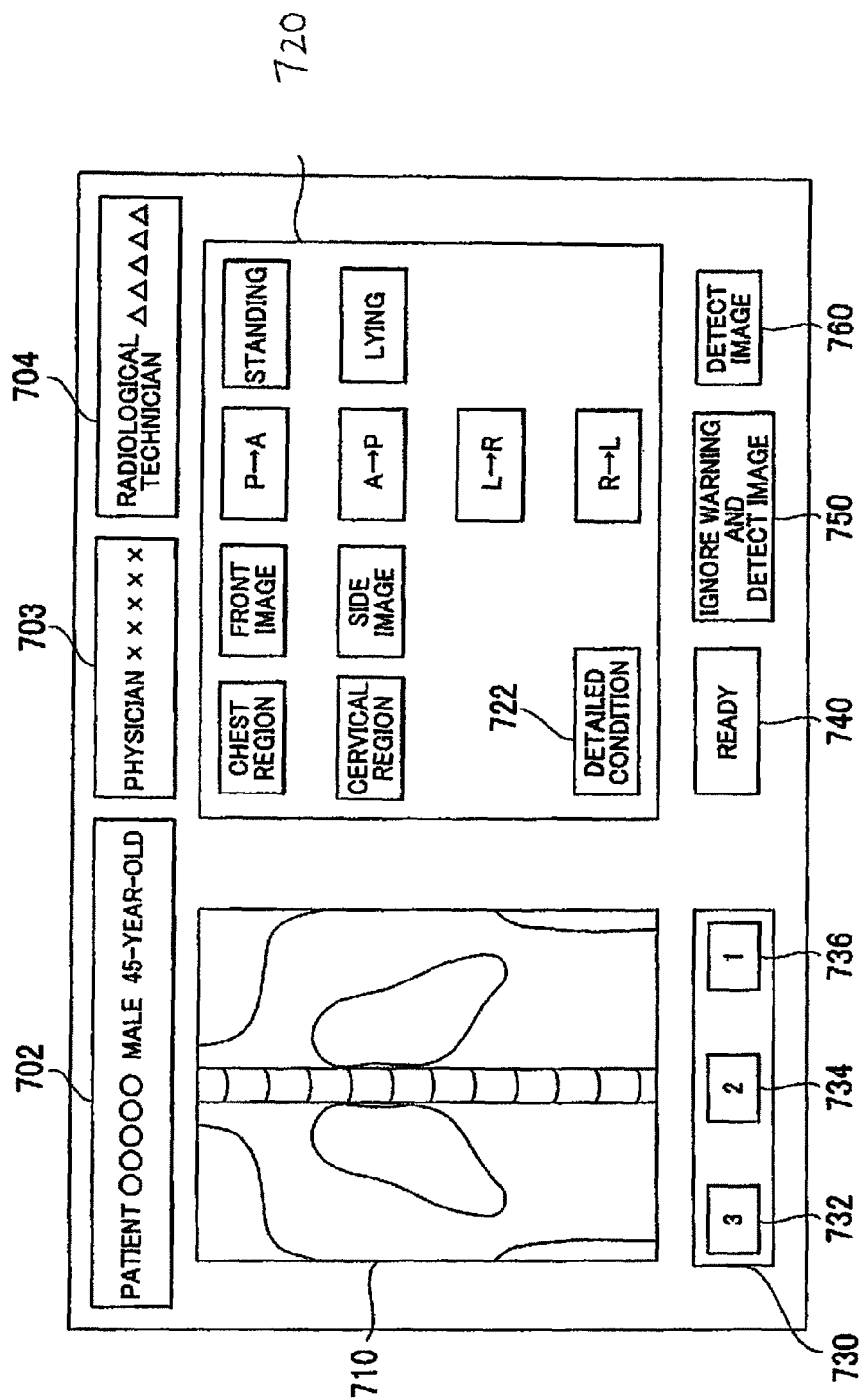
FIG. 7 illustrates an exemplary display screen displayed on a display section 260.

FIG. 7 illustrates an exemplary display screen displayed on the display section 260. Specifically speaking, FIG. 7 shows an exemplary display screen displayed on the monitor 140 of the radiation image detecting apparatus 110. The display section 260 displays thereon a display screen including an examined person display region 702, a physician in charge display region 703, a technician in charge display region 704, an image display region 710, an image detecting information input region 720, an appropriateness level region 730, a ready instruction input region 740, a warning ignoring instruction input region 750, and an image detecting instruction input region 760. The appropriateness level region 730 includes therein appropriateness level display regions 732, 734 and 736 respectively showing different appropriateness levels.

The examined person display region 702 displays therein information about the examined person. The physician in charge display region 703 displays therein information about the physician 190 who reads the radiation image of the examined person. The technician in charge display region 703 displays therein information about the radiological technician 180 who detects the radiation image of the patient.

The display section 260 also functions as the input section 210 when provided with the touch panel function for detecting the region touched by the finger of the radiological technician 180. To be specific, the radiological technician 180 inputs the site to be image-detected (for example, the cervical spine, the chest region, or the like) and the image detecting direction (for example, P→A, A→P, or the like) by touching the corresponding regions included in the image detecting information input region 720 with his/her finger. The image detecting information input region 720 includes therein a detailed condition input region 722. When the radiological technician 180 touches the detailed condition input region 722 with his/her finger, the display section 260 displays thereon an input menu to enable the radiological technician 180 to input the image detecting condition including the above-mentioned tube current, tube voltage, aperture diameter, radiation duration, and distance. The radiological technician 180 can input the image detecting condition by using an input method of, for example, touching appropriate regions with his/her finger, which is similar to the input method of the site to be image-detected and the image detecting direction through the image detecting information input region 720. Therefore, the input method of the image detecting condition is not mentioned here.

The detailed image detecting condition input by the radiological technician 180 is stored on the memory. When the ready instruction input region 740 is touched, the designated image detecting condition is transmitted from the radiation generating apparatus 130 to the server 170. The server 170 then judges whether the designated image detecting condition is appropriate. When judging that the image detecting condition received from the radiation generating apparatus 130 is inappropriate, the server 170 transmits an image stored in association with the corresponding image detecting condition to the radiation generating apparatus 130. The display section 260 displays in the image display region 710 the image received from the server 170. When the server 170 judges that the image detecting condition received from the radiation generating apparatus 130 is inappropriate, the display section 260 causes the inappropriateness level display region 736 in the appropriateness level region 730 to be displayed brighter than the other regions 732 and 734, to issue warning to the radiological technician 180 which indicates that the designated image detecting condition is inappropriate.

In response to the warning indicating that the designated image detecting condition is inappropriate, the radiological technician 180 reconsiders the image detecting condition. When concluding that the designated image detecting condition is appropriate and deciding to ignore the warning and to detect the radiation image, the radiological technician 180 touches the warning ignoring instruction input region 750, in order to instruct the radiation generating apparatus 130 to generate radiation and instruct the cassette 120 to detect the radiation. In this way, a radiation image is detected.

When the server 170 judges that the designated image detecting condition is appropriate, the display section 260 may receive the appropriateness level from the server 170 and causes one of the appropriateness level display regions 732 and 734 which corresponds to the received appropriateness level to be illuminated. In this way, the radiological technician 180 may be notified of the appropriateness level associated with the designated image detecting condition.

FIG. 7 illustrates an example of the display screen of the monitor 140 of the radiation image detecting apparatus 110. Here, the monitor 160 of the diagnosis apparatus 115 can display thereon contents similar to the contents of the display screen shown in FIG. 7. For example, the monitor 160 can display thereon information similar to the information that is mentioned in the above section as the contents displayed on the monitor 140, in the regions therein corresponding to the examined person display region 702, the physician in charge display region 703, the technician in charge display region 704 and the image display region 710. The region corresponding to the image detecting information input region 720 displays therein the image detecting information for the detected image. For example, when the image display region 710 displays therein a chest X-ray image, the chest region is illuminated in the region corresponding to the image detecting information input region 720 to inform the physician 190 that the site that has been image-detected is the chest region. The region corresponding to the detailed condition input region 722 is used as an input region to receive an instruction to display a display menu of the image detecting condition. The regions corresponding to the appropriateness level display regions 732, 734 and 736 in the appropriateness level region 730 are used to enable the physician 190 to input the appropriateness levels. The regions on the monitor 160 corresponding to the ready instruction input region 740, warning ignoring instruction input region 750, and image detecting instruction input region 760 may be used to display a selection input menu for selecting a radiation image of a different patient or a different radiation image of the same patient and causing the selected radiation image to be displayed in the image display region 710.

Figure 8:
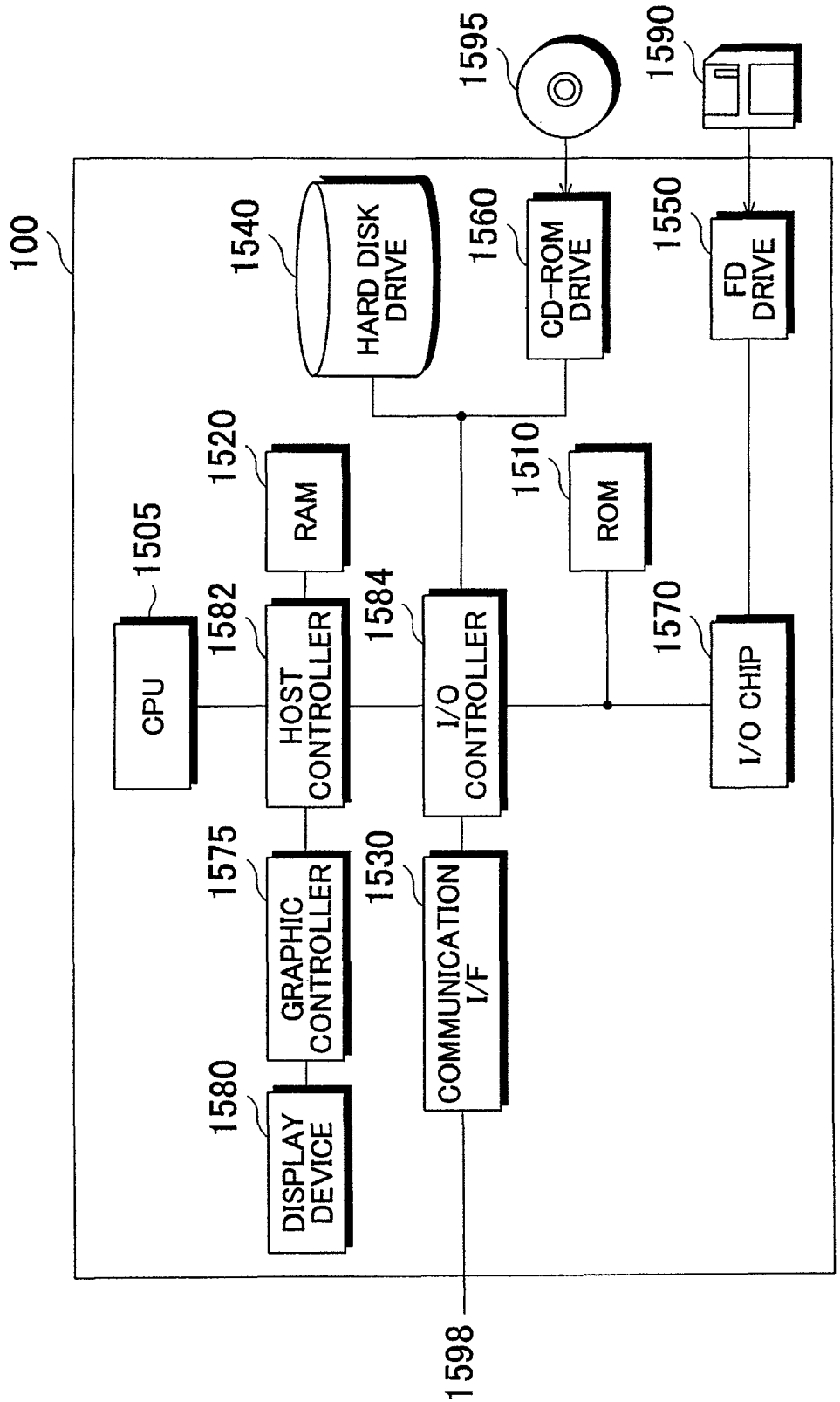
FIG. 8 illustrates an exemplary hardware configuration of the radiation image detecting system 100.

FIG. 8 illustrates an exemplary hardware configuration of the radiation image detecting system 100. The radiation image detecting system 100 is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The hard disk drive 1540 stores thereon programs and data to be used by the CPU 1505. The communication interface 1530 couples to the network communication apparatus 1598, to transmit/receive programs or data. The CD-ROM drive 1560 reads programs or data from a CD-ROM 1595, and supplies the read programs or data to the hard disk drive 1540 and communication interface 1530 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the radiation image detecting system 100 at the start up, programs unique to the hardware of the radiation image detecting system 100, and the like. The flexible disk drive 1550 reads programs or data from a flexible disk 1590, and supplies the read programs or data to the hard disk drive 1540 and communication interface 1530 via the RAM 1520. The I/O chip 1570 is used to connect a variety of I/O devices such as the flexible disk drive 1550 via, for example, a parallel port, a serial port, a keyboard port, a mouse port or the like.

The program to be executed by the CPU 1505 is provided by a user in the state of being stored on a recording medium such as the flexible disk 1590, the CD-ROM 1595, and an IC card. The program may be stored on the recording medium in the state of being compressed or not being compressed. The program is installed from the recording medium onto the hard disk drive 1540, read by the RAM 1520, and executed by the CPU 1505.

The program executed by the CPU 1505 causes the radiation image detecting system 100 to function as the input section 210, image detecting information designating section 220, image detecting information obtaining section 230, radiation image detecting section 240, image detecting control section 250, display section 260, warning section 270 and condition storing section 280, described with reference to FIGS. 1 to 7.

The program mentioned above may be stored on an external recording medium. The recording medium is, for example, an optical recording medium such as DVD and PD, a magnet-optical recording medium such as MD, a tape medium, a semiconductor memory such as an IC card and the like, in addition to the flexible disk 1590 and CD-ROM 1595. The recording medium may be a storage device such as a hard disk or RAM which is provided in a server system connected to a dedicated communication network or the Internet, and the program may be provided to the radiation image detecting system 100 via the network.

Although some aspects of the present invention have been described by way of the exemplary embodiment, it should be understood that those skilled in the art might make many changes and substitutions without departing from the spirit and the scope of the present invention which is defined only by the appended claims.

What is claimed is:
1. A radiation image detecting system comprising:
an image detecting information storing section that stores thereon an image detecting condition under which a radiation image which is judged by a reader of the radiation image to be inappropriate is detected;
an image detecting information designating section that, before a radiation image of an examined subject is detected, designates an image detecting condition under which the radiation image of the examined subject is to be detected; and
a warning section that issues warning to a user when the image detecting condition designated by the image detecting information designating section falls within a predetermined range including the image detecting condition stored on the image detecting information storing section; and a condition storing section that stores thereon an inappropriate condition, wherein the image detecting information storing section stores a number of hits indicating a number of times at which the image detecting condition designated by the image detecting information designating section is judged to fall within the inappropriate condition stored on the condition storing section, and wherein as the number of hits stored on the image detecting information storing section increases, when the image detecting condition designated by the image detecting information designating section falls within a condition which indicates an accordingly greater range than the inappropriate condition, the warning section issues warning to the user.

2. The radiation image detecting system as set forth in claim 1, wherein the image detecting information storing section stores thereon a plurality of image detecting conditions which are judged to be inappropriate, and when the image detecting condition designated by the image detecting information designating section falls within a range indicated by the plurality of image detecting conditions stored on the image detecting information storing section, the warning section issues warning to the user.

3. The radiation image detecting system as set forth in claim 1, wherein the image detecting information storing section stores thereon the image detecting condition which is judged to be inappropriate, in association with the radiation image which is detected under the image detecting condition judged inappropriate, and when the image detecting condition designated by the image detecting information designating section falls within the predetermined range including the image detecting condition stored on the image detecting information storing section, the warning section additionally presents, for a radiologist or technologist, the radiation image stored on the image detecting information storing section in association with the image detecting condition.

4. The radiation image detecting system as set forth in claim 1, wherein the image detecting information designating section designates the image detecting condition under which the radiation image of the examined subject is to be detected and a site of the examined subject which is to be image-detected, before the radiation image of the examined subject is detected, the image detecting information storing section stores thereon the image detecting condition which is judged to be inappropriate, in association with a site whose radiation image is detected under the image detecting condition judged inappropriate, and when the image detecting condition designated by the image detecting information designating section falls within a predetermined range including an image detecting condition stored on the image detecting information storing section in association with the site designated by the image detecting information designating section, the warning section issues warning to the user.

5. The radiation image detecting system as set forth in claim 1, wherein the image detecting information designating section designates the image detecting condition under which the radiation image of the examined subject is to be detected and examined subject identifying information identifying the examined subject, before the radiation image of the examined subject is detected, the image detecting information storing section stores thereon the image detecting condition which is judged to be inappropriate, in association with examined subject identifying information identifying an examined subject whose radiation image is detected under the image detecting condition judged inappropriate, and when the image detecting condition designated by the image detecting information designating section falls within a predetermined range including an image detecting condition stored on the image detecting information storing section in association with the examined subject identifying information designated by the image detecting information designating section, the warning section issues warning to the user.

6. The radiation image detecting system as set forth in claim 1, wherein the image detecting information designating section designates radiologist/technologist identifying information identifying a radiologist/technologist who is to take the radiation image of the examined subject, before the radiation image of the examined subject is detected, the image detecting information storing section stores thereon the image detecting condition which is judged to be inappropriate, in association with radiologist/technologist identifying information identifying a radiologist or technologist who takes the radiation image under the image detecting condition judged inappropriate, and when the image detecting condition designated by the image detecting information designating section falls within a predetermined range including an image detecting condition stored on the image detecting information storing section in association with the radiologist/technologist identifying information designated by the image detecting information designating section, the warning section issues warning to the user.

7. The radiation image detecting system as set forth in claim 1, wherein the image detecting information designating section designates image detecting device identifying information identifying an image detecting device used to detect the radiation image of the examined subject, before the radiation image of the examined subject is detected, the image detecting information storing section stores thereon the image detecting condition which is judged to be inappropriate, in association with image detecting device identifying information identifying an image detecting device used to detect the radiation image under the image detecting condition judged inappropriate, and when the image detecting condition designated by the image detecting information designating section falls within a predetermined range including an image detecting condition stored on the image detecting information storing section in association with the image detecting device identifying information designated by the image detecting information designating section, the warning section issues warning to the user.

8. The radiation image detecting system as set forth in claim 1, further comprising:

a radiation image detecting section that detects the radiation image by means of radiation passing through the examined subject;

an image detecting information obtaining section that obtains an image detecting condition under which the radiation image is detected by the radiation image detecting section; and a receiving section that receives, from the user, inappropriateness information indicating that the image detecting condition under which the radiation image is detected by the radiation image detecting section is inappropriate, wherein when the receiving section receives the inappropriateness information, the image detecting information storing section stores thereon the image detecting condition obtained by the image detecting information obtaining section.

9. The radiation image detecting system as set forth in claim 8, wherein the receiving section receives the inappropriateness information indicating that the image detecting condition under which the radiation image is detected by the radiation image detecting section is inappropriate, from a reader of the radiation image, when the receiving section receives the inappropriateness information, the image detecting information storing section stores thereon the image detecting condition obtained by the image detecting information obtaining section in association with reader identifying information identifying the reader who inputs the inappropriateness information, the image detecting information designating section designates reader identifying information identifying a reader who is to read the radiation image, before the radiation image of the examined subject is newly detected, and when the image detecting condition designated by the image detecting information designating section falls within a predetermined range including an image detecting condition stored on the image detecting information storing section in association with the reader identifying information designated by the image detecting information designating section, the warning section issues warning to the user.

10. A radiation image detecting method comprising:

storing an image detecting condition under which a radiation image which is judged by a reader of the radiation image to be inappropriate is detected;

before a radiation image of an examined subject is detected, designating an image detecting condition under which the radiation image of the examined subject is to be detected; and issuing warning to a user when the image detecting condition designated in the designating step falls within a predetermined range including the image detecting condition stored in the storing step; and storing an inappropriate condition, wherein the step of storing an image detecting condition includes a step of storing a number of hits indicating a number of times at which the image detecting condition is judged to fall within the inappropriate condition stored, and wherein as the number of hits stored increases, when the image detecting condition falls within a condition which indicates an accordingly greater range than the inappropriate condition, a warning is issued to the user.

11. A non-transitory computer readable medium storing thereon a program for use with a radiation image detecting apparatus, the program causing the radiation image detecting apparatus to function as:

an image detecting information storing section that stores thereon an image detecting condition under which a radiation image which is judged by a reader of the radiation image to be inappropriate is detected;

an image detecting information designating section that, before a radiation image of an examined subject is detected, designates an image detecting condition under which the radiation image of the examined subject is to be detected; and a warning section that issues warning to a user when the image detecting condition designated by the image detecting information designating section falls within a predetermined range including the image detecting condition stored on the image detecting information storing section; and a condition storing section that stores thereon an inappropriate condition, wherein the image detecting information storing section stores a number of hits indicating a number of times at which the image detecting condition designated by the image detecting information designating section is judged to fall within the inappropriate condition stored on the condition storing section, and wherein as the number of hits stored on the image detecting information storing section increases, when the image detecting condition designated by the image detecting information designating section falls within a condition which indicates an accordingly greater range than the inappropriate condition, the warning section issues warning to the user.

12. A non-transitory computer program product having computer instructions, recorded on a non-transitory computer readable medium, for enabling a computer executing the computer instructions to cause a radiation image detecting apparatus to function as:

an image detecting information storing section that stores thereon an image detecting condition under which a radiation image which is judged by a reader of the radiation image to be inappropriate is detected;

an image detecting information designating section that, before the radiation image of an examined subject is detected, designates an image detecting condition under which a radiation image of the examined subject is to be detected; and a warning section that issues warning to a user when the image detecting condition designated by the image detecting information designating section falls within a predetermined range including the image detecting condition stored on the image detecting information storing section; and a condition storing section that stores thereon an inappropriate condition, wherein the image detecting information storing section stores a number of hits indicating a number of times at which the image detecting condition designated by the image detecting information designating section is judged to fall within the inappropriate condition stored on the condition storing section, and wherein as the number of hits stored on the image detecting information storing section increases, when the image detecting condition designated by the image detecting information designating section falls within a condition which indicates an accordingly greater range than the inappropriate condition, the warning section issues warning to the user.

* * * * *